United States Patent [19]

Drent

[11] 4,382,148

[45] May 3, 1983

[54] PROCESS FOR THE PREPARATION OF GLYCOL ALDEHYDE

[75] Inventor: Eit Drent, Amsterdam, Netherlands

[73] Assignee: Shell Oil Company, Houston, Tex.

[21] Appl. No.: 315,681

[22] Filed: Oct. 27, 1981

[30] Foreign Application Priority Data

Mar. 24, 1981 [GB] United Kingdom ................. 8109119

[51] Int. Cl.$^3$ ............................................. C07C 45/49
[52] U.S. Cl. ..................................... 568/462; 568/458
[58] Field of Search ........................ 568/462, 458, 487

[56] References Cited

U.S. PATENT DOCUMENTS 3,920,753 11/1975 Yukawa et al. ..................... 568/458
4,200,765 4/1980 Goetz ................................. 568/462

Primary Examiner—Werren B. Lone

[57] ABSTRACT

A process for the preparation of glycol aldehyde, which comprises reacting formaldehyde with hydrogen and carbon monoxide, in the presence of a catalyst system derived from a rhodium-containing catalyst precursor and/or a cobalt-containing catalyst precursor together with a strong protonic acid.

8 Claims, No Drawings

PROCESS FOR THE PREPARATION OF GLYCOL ALDEHYDE

FIELD OF THE INVENTION

This invention relates to a process for the preparation of glycol aldehyde.

BACKGROUND OF THE INVENTION

U.S. Pat. No. 3,920,753 discloses that glycol aldehyde, which is a useful intermediate for the preparation of ethylene glycol, which is itself an extremely valuable commercial chemical, can be prepared by the reaction of formaldehyde with carbon monoxide and hydrogen in the presence of a cobalt catalyst. U.S. Pat. No. 4,200,765 and European Patent Application No. 2908, both disclose that this same chemical reaction can be carried out using a rhodium catalyst instead of a cobalt catalyst.

These prior art processes suffer from the disadvantage that much methanol is produced as a result of the hydrogenation of formaldehyde which proceeds as a side-reaction. In order to suppress the methanol production to a reasonable level, the prior art processes use very high pressures; in addition, they use carbon monoxide/hydrogen gas mixtures with a relatively high carbon monoxide content.

It has now been found that the production of glycol aldehyde in this type of process, when using either a cobalt or a rhodium catalyst, can be improved by the addition to the reaction mixture of a catalytic amount of a strong protonic acid. In particular, the quantity of methanol formed can be much reduced.

SUMMARY OF THE INVENTION

The invention therefore provides a process for the preparation of glycol aldehyde, which comprises reacting formaldehyde with hydrogen and carbon monoxide, in the presence of a catalyst system derived from a rhodium-containing catalyst precursor and/or a cobalt-containing catalyst precursor together with a strong protonic acid.

DESCRIPTION OF THE PREFERRED EMBODIMENTS

The catalyst precursor used in the process according to the invention comprises rhodium and/or cobalt in any form generally used in catalytic reactions. The precursor may, for example be a salt of rhodium or cobalt with a mineral acid, for example a halide, nitrate or sulphate, or with an organic acid, for example a carboxylate having up to 20 carbon atoms, especially an alkanoate, such as an acetate. Alternatively, the metal may be in zero valent form, optionally complexed by ligands such as the phosphine ligands described below, carbon monoxide, or acetylacetonates. Frequently both anions and uncharged ligands are present, e.g. as in [Rh.Cl(CO)$_2$]. The precise form of the active catalyst in the process of the invention is not known; in some cases the rhodium- or cobalt-containing catalyst precursor added to the reaction mixture will itself function directly as a catalyst, in others it will be converted into an active form in situ.

The quantity of rhodium or cobalt present in the reaction mixture is generally determined by economic considerations. Quantities of rhodium and/or cobalt of between 0.001 to 10%, especially 0.01 to 5%, calculated as gram atoms of metal per mole of formaldehyde used as feedstock, are generally suitable. Generally rhodium is more active as a catalyst than cobalt, but the use of cobalt may be desirable because of its relatively low cost. In certain cases, a catalyst system containing both rhodium and cobalt may be useful.

The strong protonic acid used in the process according to the invention may be an organic acid, for example a sulphonic acid such as p-toluene sulphonic acid, methane sulphonic acid, naphthalene sulphonic acid or trifluoromethane sulphonic acid, or an alkanoic acid substituted by at least one electron-withdrawing moiety, for example haloalkanoic acids such as trichloroacetic acid; or an inorganic acid, for example a hydrohalic acid, sulphuric acid, or perchloric acid. The acid may be homogeneous with the reaction medium, or it may be a solid; for example, protons may conveniently be provided by a suitable strongly acidic ion exchange resin. In general, suitable homogeneous acids are those which in aqueous solution at 20° C. have a pKa of less than 3.5, preferably less than 2.5. Suitable ion-exchange resins are those of equivalent acid strength, for example the acidic NAFION (Trade Mark) or AMBERLITE (Trade Mark) resins, which contain, respectively, polyfluoroalkyl sulfonic acid groups, and aryl sulfonic acid groups. Equally suitable acidic ion-exchange resins are those which contain phosphonic acid groups. Only a catalytic quantity of acid is required in order to increase the selectivity of the reaction to glycol aldehyde, and indeed large quantities of acid are undesirable as they can cause polymerization of the glycol aldehyde product. Suitably the maximum number of acid equivalents added per gram atom of rhodium and/or cobalt is 100; preferably the number of acid equivalents added per gram atom of rhodium and/or cobalt is within the range of from 0.1 to 20, especially 0.5 to 10. Thus, as used herein, the term "strong protonic acid" shall refer to a homogeneous acid which in aqueous solution at 20° C. has a pKa of less than 3.5, preferably less than 2.5 or to an acidic ion-exchange resin which contains sulfonic acid or phosphonic acid moieties attached thereto.

In general, although the hydrohalic acids are extremely effective when used in the process according to the invention, it may be preferred to use a halide-free acid, since halide ions tend to be corrosive, causing problems in maintaining equipment. For the same reason, the use of a halide-free rhodium or cobalt catalyst precursor may be advantageous.

The formaldehyde starting material may be introduced into the reaction zone in any suitable form, and it may be generated in situ. Paraformaldehyde is a convenient source. Commercial formaldehyde often contains varying quantities of either methanol or water, depending on how the material has been synthesized, and the process according to the invention can be carried out successfully using such feedstocks.

The molar ratio of the carbon monoxide to hydrogen supplied to the system is not critical and may vary over a wide range, for example about 5:95 to about 95:5, preferably about 30:70 to about 80:20. It is generally preferred to use a gas stream in which the molar ratio of CO:H$_2$ is at least 1:1, since under such conditions the hydrogenation of formaldehyde to methanol is minimized. The reaction is conducted under pressure, for example at a pressure in the range of from about 5 to about 200, especially about 25 to about 80, bars. Higher pressures may of course be used, but are generally uneconomical, and it is one of the advantages of the present invention that it enables relatively low pressures to be used. Inert gases may also be present in the gas stream, but as this leads to an increase in total pressure, it is generally undesirable. The reaction is preferably conducted at a temperature in the range of from about 30° C. to about 200° C., especially about 50° C. to about 130° C. The use of a temperature as low as possible commensurate with the desired rate of reaction is preferred, since at higher temperatures, the glycol aldehyde product tends to polymerize.

The process according to the invention is suitably carried out in the presence of a solvent. Details of suitable solvents for reactions of this kind may be found in the prior art noted above, incorporated by reference herein, for example, as described in European Patent Application No. 2908, solvents having multiple bonds from carbon to other atoms, for example as in nitriles or pyridine, are generally suitable. N,N-disubstituted amides have proved to be especially suitable solvents, optionally in admixture with co-solvents, since they apparently exert a promoting effect on the reaction. If it is desired to extract the glycol aldehyde product from the reaction mixture using water, it is convenient to use a water-immiscible amide as solvent. Suitable water-immiscible amides are those containing long-chain alkyl moieties. Alternatively, if an amide which is wholly or partially miscible with water is used, for example N,N-dimethylformamide, N,N,-dimethylacetamide or a cyclic amide such as N-methylpyrrolidone, it may be convenient to use a water-immiscible co-solvent such as benzene. In this case, extraction by water removes the glycol aldehyde together with at least some of the amide, leaving the rhodium or cobalt in solution in the hydrophobic co-solvent.

Although not essential for the process according to the invention, the use of a promotor in conjunction with the catalyst system is highly desirable. Suitable promotors commonly used in catalytic reactions are organo oxygen, nitrogen, phosphorus, arsenic and antimony compounds having a lone pair of electrons. Preferred promotors are organo nitrogen or, especially, organo phosphorus compounds. Suitable oxygen-containing promotors include compounds containing a hydroxy, carbonyl, carbonyloxy or ether groups. Typical compounds of this type include carboxylic acids, especially hydroxy or alkoxy substituted acids, such as methoxyacetic acid or hydroxyacetic acid, ethers such as tetrahydrofuran, and amides, such as dimethylacetamide. Amides are of course an example of a promotor containing both nitrogen and oxygen atoms, and, as stated above, amides have proved to be especially useful solvents for the process according to the invention.

Suitable phosphorus, antimony and arsenic promotors include those of the general formula XR'R''R''', in which X represents phosphorus, antimony or arsenic, and each of R',R'' and R''' independently represents an optionally substituted alkyl, cycloalkyl or aryl group, or R' has this meaning and R'' and R''' together represent an alkylene group. Optional substituents may be any moieties inert under the reaction conditions, for example halogen atoms, alkoxy groups, phenyl groups, and groups of formula XR'R''. Preferably however, R' and R'' are hydrocarbyl groups and R''' is a hydrocarbyl group or a group $CH_2XR'R''$ where R' and R'' are hydrocarbyl groups. Preferably any alkyl group has up to 20 carbon atoms; any cycloalkyl group has up to 7 carbon atoms; any aryl group is a phenyl group; and any alkylene group has up to 20 carbon atoms. Especially preferred promotors of this type are those in which each of R', R'' and R''' independently represents an alkyl group or a phenyl group. For economic reasons, it is generally preferred that each of R', R'' and R''' represents the same group. Preferably X represents a phosphorus atom. Typical phosphine promotors are trimethylphosphine, triethylphosphine, tributylphosphine, triphenylphosphine, and $(phenyl)_2PCH_2P(phenyl)_2$. The use of triphenylphosphine is especially preferred. Suitable nitrogen-containing promotors include those of the general formula NR'R''R''' where R', R'' and R''' have the meanings given above, and also compounds in which the nitrogen atom forms part of a heterocyclic ring. Typical promotors of this type include pyrrole, pyrrolidine, pyridine, piperidine, pyrimidine, picoline and quinoline, and analogues thereof, for example alkyl-substituted analogues. The amount of promotor used is not critical. Except in those cases where the promotor or one of the promotors used is employed as a solvent, the ratio of promotor to catalyst is preferably in the range of from about 1:1 to about 20:1, especially about 2:1 to about 10:1, calculated as moles of promotor per gram atom of rhodium and/or cobalt. In an especially preferred embodiment of the process according to the invention, an amide is used as solvent or co-solvent and in addition a phosphorus-containing promotor is present.

The main use of glycol aldehyde is its conversion to ethylene glycol by catalytic hydrogenation. Under certain reaction conditions, some or all of the glycol aldehyde prepared by the process according to the invention may be hydrogenated in situ over the rhodium or cobalt catalyst to produce ethylene glycol, and the present invention should be understood to include the preparation of glycol aldehyde which is converted in situ into other products.

In general, however, reaction conditions which tend to favor the hydrogenation of glycol aldehyde immediately as it is formed, tend also to favor the hydrogenation of the formaldehyde starting material to methanol. Usually therefore the highest overall yields of ethylene glycol are obtained by preparing glycol aldehyde under reaction conditions which minimize hydrogenation, and subsequently hydrogenating the glycol aldehyde product in a second reaction step.

The rhodium or cobalt catalyst systems used in the process of the present invention are relatively inefficient hydrogenation catalysts, and it is preferred to use a more active hydrogenation catalyst for the subsequent hydrogenation step. Such catalysts are well known; for example palladium, platinum or nickel catalysts, often in heterogeneous form, are commonly used. The selected hydrogenation catalyst may be added directly to the reaction mixture after completion of the preparation of glycol aldehyde with no work-up procedure and gaseous hydrogen introduced. Hydrogen gas which is free from substantial quantities of carbon monoxide is of course a preferred reactant when using a hydrogenation catalyst which is poisoned by carbon monoxide. Alternatively, the reaction mixture resulting from the preparation of glycol aldehyde may be worked up before the glycol aldehyde is hydrogenated. For example the glycol aldehyde may be extracted using a suitable solvent. As described above, water is a convenient extractant. A further convenient extractant is ethylene glycol itself. The resulting solution may then be hydrogenated in conventional manner.

ILLUSTRATIVE EMBODIMENTS

The following Examples are provided to illustrate the invention and are not intended to be construed as limiting the invention.

EXAMPLES

All the Examples were carried out using the following general method. A Hastelloy C (Trade Mark) 300 ml magnet-driven autoclave was charged with 0.25 moles formaldehyde in the form of paraformaldehyde, 50 mls of the chosen solvent, (except Examples 11 and 13, 55 and 58 mls) and the necessary catalyst components. The autoclave was then flushed with carbon monoxide and pressurized to a working pressure of 60 bars (except Example 6, where the pressure was 50 bars) with a carbon monoxide/hydrogen mixture. The pressure was maintained throughout the reaction by feeding in the $CO/H_2$ mixture as required. After the required reaction temperature and pressure had been maintained for the required reaction time, the contents of the autoclave were cooled and analyzed using gas-liquid chromatography. In Examples 1, 2, 3 and 17, a $CO:H_2$ mixture of 2:1 molar was used, in all other Examples a $CO:H_2$ mixture of 1:1 molar was used. In Example 7, the ratio of glycol aldehyde to methanol was not measured because of the presence of methanol in the solvent used, and in Example 15, the exact yield of glycol aldehyde was not determined because the reaction mixture contained solid material.

All the acids added were used in the form of their usual laboratory concentrated solutions. In the case of HCl, this is a 37% aqueous solution.

The following abbreviations have been used: "DMF"—dimethylformamide; "DMA"—dimethylacetamide; "acac"—the acetylacetonate ligand. The results of Examples 1 to 15 are given in the following Table, where the selectivity of the reaction is calculated as:

$$\frac{\text{moles glycol aldehyde}}{\text{moles glycol aldehyde + methanol}} \times 100\%.$$

TABLE OF RESULTS

| Example No. | Catalyst Components (mmol) | Solvent | Temperature (°C.) | Time (Hours) | Selectivity (% m) | Yield glycol aldehyde calculated on formaldehyde intake (% m) |
|---|---|---|---|---|---|---|
| 1 | [RhCl(CO)$_2$]$_2$ (0.25) HClO$_4$ (0.5) P(phenyl)$_3$ (2.0) | DMF | 115 | 3 | 68 | 37 |
| 2 | [RhCl(CO)$_2$]$_2$ (0.25) HCl (0.6) P(phenyl)$_3$ (2.0) | DMF | 115 | 3 | 92 | 60 |
| 3 | [RhCl(CO)$_2$]$_2$ (0.25) HCl (0.5) P(phenyl)$_3$ (2.0) | DMF + 2% water | 115 | 3 | 85 | 50 |
| 4 | [RhCl(CO)$_2$] (0.25) H$_2$SO$_4$ (0.5) P(phenyl)$_3$ (2.0) | DMF | 115 | 3 | 71 | 43 |
| 5 | [RhCl(CO)$_2$]$_2$ (0.25) HCl (0.5) P(phenyl)$_3$ (2.0) | DMA | 100 | 15 | 95 | 80 |
| 6 | [RhCl(CO)$_2$]$_2$ (0.25) HCl (0.5) P(phenyl)$_3$ (2.0) | DMA | 100 | 15 | 95 | 77 |
| 7 | [RhCl(CO)$_2$]$_2$ (0.25) HCl (0.5) P(phenyl)$_3$ (2.0) | DMA + 5% methanol | 100 | 15 | Not measured | 40 |
| 8 | Rh acac (CO)$_2$ (0.5) HCl (0.5) P(phenyl)$_3$ (2.0) | DMA | 100 | 15 | 93 | 73 |
| 9 | Rh acac (CO)$_2$ (0.5) p-toluene sulfonic acid (4.0) P(phenyl)$_3$ (2.0) | DMA | 90 | 3 | 96 | 55 |
| 10 | Rh acac (CO)$_2$ (1.0) naphthalene sulfonic acid (4.0) P(phenyl)$_3$ (2.0) | DMA | 85 | 5 | 88 | 40 |
| 11 | Rh acac (CO)$_2$ (1.0) p-toluene sulfonic acid (4.0) P(phenyl)$_3$ (2.0) | 15 mls DMA 40 mls benzene | 85 | 4 | 94 | 30 |
| 12 | Co$_2$(CO)$_8$ (1.0) p-toluene sulfonic acid (4.0) P(phenyl)$_3$ (2.0) | DMA | 93 | 5 | 93 | 28 |
| 13 | [RhCl(Co)$_2$]$_2$ (0.25) HCl (0.5) P(phenyl)$_3$ (2.0) | 50 mls DMA 8 mls pyridine | 100 | 15 | 90 | 23 |
| 14 | Rh acac (CO)$_2$ (0.5) p-toluene sulfonic acid (4.0) P(phenyl)$_3$ (2.0) | pyridine | 88 | 3 | 85 | 50 |
| 15 | Rh acac (CO)$_2$ (0.5) p-toluene sulfonic acid (4.0) | acetonitrile | 85 | 15 | 95 | >20 |

TABLE OF RESULTS-continued

| Example No. | Catalyst Components (mmol) | Solvent | Temperature (°C.) | Time (Hours) | Selectivity (% m) | Yield glycol aldehyde calculated on formaldehyde intake (% m) |
| --- | --- | --- | --- | --- | --- | --- |
| | P(phenyl)$_3$ (2.0) | | | | | |

EXAMPLE 16

In this Example, the catalyst components used were [RhCl(CO)$_2$]$_2$ (1.0 mmol), triphenylphosphine (2.0 mmols) and 0.8 g of a sulfonic acid type solid acidic ion exchange resin Amberlite 252+ (Trade Mark). The solvent was DMA. After 5 hours at a temperature of 85° C., the selectivity to glycol aldehyde was 60%, and the overall yield of glycol aldehyde based on formaldehyde was 20% m.

EXAMPLE 17

The procedure of Examples 1 and 2 was repeated exactly except that no HCl or HClO$_4$ was added to the reaction mixture. The selectivity to glycol aldehyde was 45%, and the yield of glycol aldehyde calculated on formaldehyde input was 25% m.

EXAMPLE 18

(Comparison)

The procedure of Example 5 was repeated except that no HCl was added. The selectivity to glycol aldehyde was 21% and the yield of glycol aldehyde calculated on formaldehyde input was 8% m.

EXAMPLE 19

Comparison)

The procedure of Example 16 was repeated except that no acidic ion exchange resin was added. The selectivity to glycol aldehyde was 36%, and the yield of glycol aldehyde calculated on formaldehyde input was 10% m.

EXAMPLE 20

(Illustration of Work-up Procedure)

The reaction mixture obtained in Example 11 was treated with water and the aqueous phase separated. More than 90% of the glycol aldehyde was present in the aqueous phase.

A similar extraction of a reaction mixture was carried out using a benzene/ethylene glycol mixture (1:1 by volume) as extractant. The bottom (ethylene glycol) layer contained more than 90% of the glycol aldehyde, while most of the catalyst was present in the top (benzene) layer. The addition of a small quantity of water gave even better catalyst separation.

EXAMPLE 21

(Illustration of the Hydrogenation of Glycol Aldehyde)

A reaction mixture containing glycol aldehyde can be worked up in numerous different ways. This Example illustrates the hydrogenation of glycol aldehyde in various model systems which might have resulted from its preparation.

Run (a). 3 g glycol aldehyde; 30 mls propane-1,2-diol; 1 g palladium on charcoal (5% by weight). Reaction at 80° C. for 5 hours under a hydrogen pressure of 50 bars gave a yield of 80% ethylene glycol.

Run (b). 4 g glycol aldehyde; 30 mls water; 1 g nickel 1404T (Trade Mark: Harshaw) catalyst. Reaction at 85° C. for 5 hours under a hydrogen pressure of 50 bars, gave a quantitative yield of ethylene glycol.

Run (c). 4 g glycol aldehyde; 24 l mls water; 6 mls DMF; 1 g nickel 1404T (Trade Mark: Harshaw) catalyst. Reaction at 80° C. for 5 hours under a hydrogen pressure of 40 bars, gave a yield of 90% ethylene glycol.

Run (d). 4 g glycol aldehyde; 30 mls N-methylpyrrolidone; 0.5 g palladium on charcoal (5% by weight). Reaction at 110° C. for 5 hours under a hydrogen pressure of 50 bars gave a yield of 75% ethylene glycol.

Run (e). 4 g glycol aldehyde; 30 mls water; 0.5 g palladium on charcoal (5% by weight); 0.4 g sodium sulfate (modelling the case of sulfuric acid present in the initial reaction mixture, neutralized by sodium hydroxide). Reaction at 85° C. for 5 hours under a hydrogen pressure of 50 bars, gave a quantitative yield of glycol aldehyde.

Run (f). 6.6 g glycol aldehyde; 50 mls water; 0.76 g p-toluene sulfonic acid. This mixture was percolated over the Na ⓡ form of an ion exchange resin. 0.5 g palladium on charcoal (5% by weight) was then added. Reaction for 5 hours at 85° C. under a hydrogen pressure of 50 bars, gave a quantitative yield of ethylene glycol.

I claim:

1. A process for the preparation of glycol aldehyde, which comprises reacting formaldehyde with hydrogen and carbon monoxide at a temperature in the range of from about 30° C. to about 200° C. and at a pressure in the range of from about 5 to about 200 bars, in the presence of a catalyst system derived from a rhodium-containing catalyst precursor and/or a cobalt-containing catalyst precursor together with a strong protonic acid.

2. The process of claim 1 wherein the strong protonic acid is an organic sulphonic acid, an alkanoic acid substituted by at least one electron-withdrawing group, a hydrohalic acid, sulfuric acid or perchloric acid.

3. The process of claim 2 wherein the strong acid is a hydrohalic acid, sulfuric acid, p-toluene sulfonic acid or naphthalene sulfonic acid.

4. The process of claim 1 in which the strong protonic acid is a strongly acidic ion exchange resin containing phosphonic or sulfonic acid moieties.

5. The process of claim 1 wherein the quantity of strong acid is such that the number of acid equivalents added per gram atom of rhodium and/or cobalt is in the range of from about 0.1 to about 20.

6. The process of claim 1 wherein the molar ratio of carbon monoxide to hydrogen is within the range of from about 30:70 to about 80:20.

7. The process of claim 1 wherein said process is carried out in a reaction medium comprising an N,N-disubstituted amide as solvent or co-solvent.

8. The process of claim 1, 2, 3, 4, 5, 6, or 7 wherein the reaction mixture additionally comprises an organo phosphorus-containing promotor.

* * * * *